US008765054B2

(12) United States Patent
Pressel et al.

(10) Patent No.: US 8,765,054 B2
(45) Date of Patent: Jul. 1, 2014

(54) PROCESS FOR TREATMENT OF RESIDUAL NUCLEIC ACIDS PRESENT ON THE SURFACE OF LABORATORY CONSUMABLES

(75) Inventors: Marie Pressel, Dachstein (FR); Didier Metz, Stotzheim (FR)

(73) Assignee: EMD Millipore Corporation, Billerica, MA (US)

( * ) Notice: Subject to any disclaimer, the term of this patent is extended or adjusted under 35 U.S.C. 154(b) by 169 days.

(21) Appl. No.: 13/275,700

(22) Filed: Oct. 18, 2011

(65) Prior Publication Data

US 2012/0095178 A1 Apr. 19, 2012

(30) Foreign Application Priority Data

Oct. 19, 2010 (FR) ...................... 10 58516

(51) Int. Cl.
| | |
|---|---|
| A61L 2/00 | (2006.01) |
| A61L 9/00 | (2006.01) |
| B08B 9/00 | (2006.01) |
| B08B 5/00 | (2006.01) |
| B08B 3/00 | (2006.01) |
| A61L 12/12 | (2006.01) |
| B01D 65/06 | (2006.01) |
| A01N 63/00 | (2006.01) |

(52) U.S. Cl.
CPC .. *A61L 2/00* (2013.01); *A61L 12/12* (2013.01); *B01D 65/06* (2013.01); *A01N 63/00* (2013.01)
USPC ... 422/28; 422/1; 422/23; 422/33; 134/22.16; 134/26; 134/31

(58) Field of Classification Search
CPC ......... A61L 12/00; A61L 12/08; A61L 12/12; A61L 12/10; A61L 2/00; A61L 2/16; A61L 101/22; B01D 65/06; A01N 63/00
USPC ........... 435/1.1, 287.2; 600/36; 422/1, 23, 28, 422/33, 186, 186.12, 305; 134/22.16, 26, 134/31
See application file for complete search history.

(56) References Cited

U.S. PATENT DOCUMENTS

| | | | | |
|---|---|---|---|---|
| 8,142,991 B2 * | 3/2012 | Mills et al. | ..................... | 435/1.2 |
| 2004/0262146 A1 * | 12/2004 | Platt et al. | ..................... | 204/164 |
| 2010/0255484 A1 * | 10/2010 | Halverson et al. | ................ | 435/6 |

FOREIGN PATENT DOCUMENTS

| | | |
|---|---|---|
| EP | 1792631 A1 | 6/2007 |
| WO | 93/20241 A1 | 10/1993 |
| WO | 2005/007884 A1 | 1/2005 |
| WO | 2007/044520 A1 | 4/2007 |

OTHER PUBLICATIONS

French Search Report dated May 16, 2011 in corresponding French Patent Application No. FR 1058516.

(Continued)

*Primary Examiner* — Monzer R Chorbaji
(74) *Attorney, Agent, or Firm* — Nields, Lemack & Frame, LLC

(57) ABSTRACT

Process for treatment of residual nucleic acids present on the surface of laboratory consumables. The process combines two treatment phases: (1) treatment with ethylene oxide in gaseous phase; then (2) treating the surface with hydrogen peroxide in liquid phase or in gaseous phase. The effect of this treatment is the avoidance of the amplification of residual nucleic acids, in particular during PCR or TMA reactions.

16 Claims, 4 Drawing Sheets

(56) References Cited

OTHER PUBLICATIONS

Figure 1:
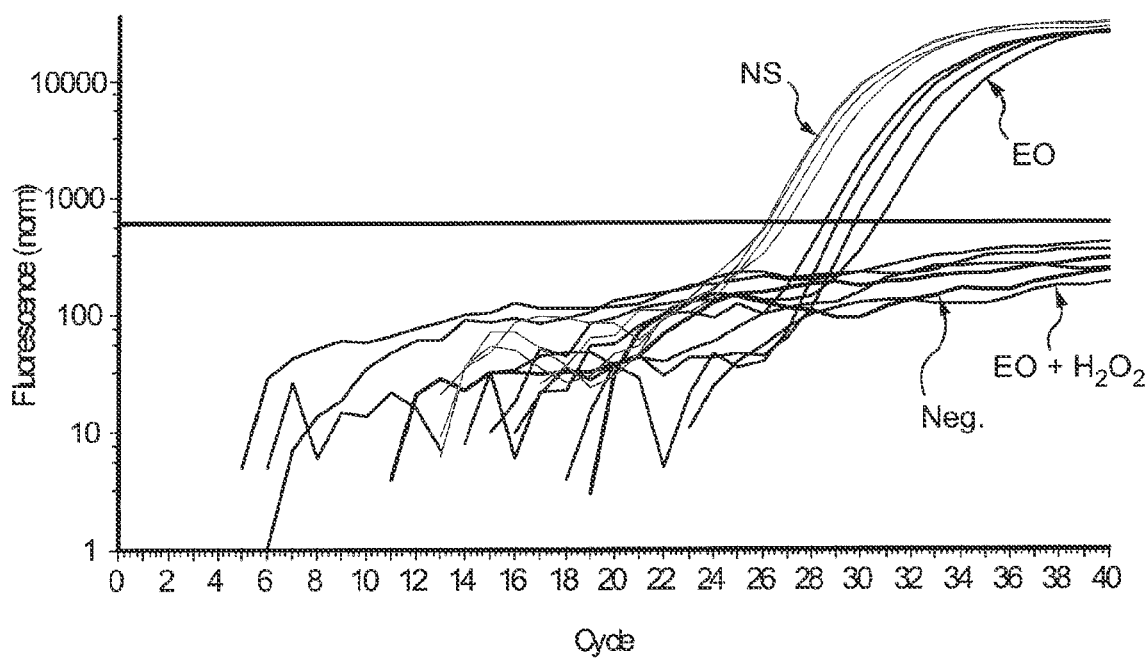

Forensic Science International: Genetics, vol. 4, No. 4, Jul. 1, 2010, pp. 239-243, XP027078777, "Validation of a dual cycle ethylene oxide treatment technique to remove DNA from consumables used in forensic laboratories", Archer, et al.

International Journal of Legal Medicine, vol. 122, No. 1, Jan. 2008, pp. 29-33, XP002636408, "Comparison of the effects of sterilisation techniques on subsequent DNA profiling", Shaw, et al.

Human Genetics, 1989, 83(1): 1-15, "The Polymerase Chain Reaction: An Improved Method for the Analysis of Nucleic Acids", Vosberg.

Naturwissenschaften, 1995, vol. 82, pp. 423-431, "Evidence of Contamination in PCR Laboratory Disposables", Schmidt, et al.

Swiss NOSO, vol. 4, No. 1, Mar. 1997, pp. 1-8, "Reduction de personnel et infections nosocomiales", Pittet, et al.

* cited by examiner

PROCESS FOR TREATMENT OF RESIDUAL NUCLEIC ACIDS PRESENT ON THE SURFACE OF LABORATORY CONSUMABLES

This application claims priority of French Patent Application No. 1058516 filed Oct. 19, 2010, the disclosure of which is incorporated herein by reference.

The present invention concerns a process for treatment of the residual nucleic acids present on the surface of consumables, more particularly laboratory consumables, in particular tubes and filters used in the experiments for amplification of DNA or RNA samples.

This invention aims to address, more particularly, the problem posed by the specific or non-specific amplification of the residual nucleic acids present on the surface of said consumables, on implementing techniques using polymerase chain reactions (PCR) or transcription mediated amplification (TMA) reactions.

These residual nucleic acids generally come from the surroundings, may be present in free form, or else be contained in living cells such as microorganisms, viruses or protozoa.

PREAMBLE

Nucleic acid amplification reactions consist of a succession of enzymatic reactions involving the action of a polymerase enabling the synthesis of new nucleic acid molecules from a nucleic acid sequence initially present in the reaction medium.

The aim of these enzymatic reactions is generally to generate copies of the same nucleic acid sequence initially present in small quantity in a sample. The most frequently used amplifications are those involving successive polymerization or transcription reactions, such as PCR and TMA. Such techniques are widely described and are well-known to the person skilled in the art. Using specific primers, they enable copying of the same nucleic acid sequence a very high number of times on the basis of a single DNA or RNA template.

In such reactions, it is the nucleotide sequence of the primers used to initiate the polymerization reaction that determines which nucleic acid sequence is to be amplified.

The nucleic acid sequences obtained by the amplification reactions are useful in numerous applications in the field of molecular biology such as gene cloning, the diagnosis of genetic diseases, or the detection of viruses or microorganisms [Vosberg, H. P., (1989) The polymerase chain reaction: an improved method for the analysis of nucleic acids, *Hum Genet.* 83(1): 1-15].

According to the conditions in which the enzymatic reactions are carried out, in particular the degree of stringency used (concentration of salts and hybridization temperature), it is possible to amplify DNA or RNA sequences whose sequence is more or less identical to that which it is sought to amplify.

To obtain a very specific amplification of a given sequence, that is to say to target solely nucleic acids having a sequence identical to that of the primers introduced into the reaction medium, conditions of high stringency should be adopted. Conversely when it is sought to amplify sequences having a certain variability relative to the primers used, the reaction conditions should be of lower stringency.

In the context of universal tests for microorganism detection, genetic investigations, or diagnosis of infectious diseases, it is frequent to have to search for nucleic acid sequences having a certain variability relative to the sequence type sought to take into account differences in sequences between individuals or species. To that end, it is often necessary to have recourse to conditions of lower stringency enabling the genetic diversity to be taken into account.

Nevertheless, the tests carried out in conditions of low stringency bear the risk of amplifying sequences coming from residual nucleic acids foreign to the sample under study. The appearance of "false positives" results therefrom, which may substantially distort the results of the tests.

In the case of the universal detection of microorganisms, the risk of false positives linked to the presence of residual nucleic acids coming from the surroundings, is very high [Schmidt, T., Hummel, S., Hermann, B., 1995, Evidence of contamination in PCR laboratory disposables; *Naturwissenschaften* 82].

In the forensic, when it is sought to establish the identity of a criminal on the basis of his genetic fingerprint, there is also a non-zero risk that tubes or the equipment used in the laboratory may be contaminated by the DNA of another person, or even by that of the operator. It is thus difficult to establish the DNA profile of the criminal with certainty.

For these reasons, it is very important for the devices dedicated to the amplification of nucleic acids to be completely rid of the amplifiable residual nucleic acids.

In general, the consumable products used in the reactions of molecular biology, including those involved in amplification reactions of DNA or RNA, are manufactured in a clean room, before undergoing a final step of conventional sterilization to ensure the absence of microbes.

These conventional sterilization methods are however not sufficient to eliminate all the amplifiable nucleic acids from the surfaces of the consumables.

Consumables free of human DNA, RNA, DNase, RNase and other inhibitors of PCR may receive the "PCR clean" label. This does not however mean that they are free from bacterial nucleic acids coming from the surroundings. Enzymes such as endonucleases or chemical products such as psoralen may be used in order to render the residual nucleic acid molecules non-amplifiable.

However, such products or enzymes can have a negative interaction with the reagents and the samples used in the amplification reactions.

Other methods for the removal of residual amplifiable nucleic acids use ionizing radiation (ultra violet (UV), gamma ($\gamma$), X-rays and beta ($\beta$)), but, to be more effective, the duration of exposure must be several hours, which makes the process costly, and, above all, degrades or weakens the materials from which the consumables are made. Furthermore, the manipulation of ionizing radiation is subject to strict regulation, which limits its possibility of implementation.

Currently, to sterilize its consumables, the applicant uses a process for treatment with hydrogen peroxide commercialized under the name Sterrad® (Johnson & Johnson). Hydrogen peroxide is an oxidizing gas which enables the destruction by oxidation of the cellular components of microorganisms, in particular proteins, and to a lesser extent nucleic acids. The Sterrad® process uses 90% hydrogen peroxide, in gaseous form, at low temperature. According to this process, a vacuum phase is applied in the chamber in which the consumables to be treated are situated, such that the gaseous phase penetrates and passes within all the parts of the devices to be treated. At the end of the cycle, a vacuum phase is again applied, whereas the molecules of hydrogen peroxide are ionized by application of an electric field and formation of a plasma. One of the advantages of the Sterrad process is that devices may be sterilized, while they are pre-packed in plastic sachets. The sachets comprise a face of non-woven synthetic (Tyvek®) that is permeable to hydrogen peroxide.

However, the applicant found that this process did not totally destroy the residual nucleic acids contained within the devices. The Sterrad® process, thus, only partially satisfies the applicant's needs.

It should be noted that the applicant is specialized in the manufacturing of membranes filtration devices comprising filter membranes intended for micro-organism detection tests. These micro-organism detection tests are typically carried out by PCR amplification after filtering a liquid sample through said devices that have been rendered sterile.

These devices often consist of complex devices comprising conduits, tanks and a filter membrane, which makes their treatment more difficult.

The applicant has applied the Sterrad® process several times over to attempt to completely eliminate the residual nucleic acids persisting in the devices. However, amplifications still remained showing that nucleic acids from microorganisms were not totally eliminated (FIG. 3B).

The applicant has thus undertaken research to improve the aforementioned processes, for the purpose of developing a process to treat the residual nucleic acids present in those devices, with the conditions of (i) not damaging the materials from which the devices are constituted, in particular, the membranes and the filters (for example: polypropylene, PES, PVDF) and (ii) not having the effect of inhibiting nucleic acid amplification reactions, for which those devices are intended.

Further to numerous tests, the applicant has determined that a two-step decontamination treatment of the surfaces to be treated allows the above mentioned conditions to be met.

The process developed comprises a first step of treatment by ethylene oxide in gaseous phase, followed by a second step of treatment with hydrogen peroxide in liquid or gaseous phase. The applicant has found that the combination of these two steps enabled a more thorough decontamination that those of the prior techniques.

In particular, the applicant found, by using comparative tests, that the effect of the two steps for treating the device was to eliminate any undesirable amplification, even when the residual nucleic acids are initially contained in microorganisms, which cannot be achieved when only one of the treatment steps is carried out.

The different modes of the invention and the advantages resulting therefrom are detailed below.

FIG. 1: A graph comparing different decontamination treatments applied to residual DNA contained initially in microorganisms (S. epidermis). The surfaces of the consumables (1.5 ml tubes) were contaminated with the same number of cells of S. epidermis before receiving the respective treatment NS (light gray): no treatment. EO (medium gray): treatment by ethylene oxide in gaseous phase. EO+$H_2O_2$ (l) (black): treatment according to the invention by ethylene oxide in gaseous phase and then by hydrogen peroxide in liquid solution (30%). Neg. (dark gray): Negative control not contaminated by S. epidermis. The surfaces so treated were then rinsed and a PCR reaction (40 cycles) was carried out on the rinse products, for the purpose of detecting possible residual DNA coming from S. epidermis. The curves represent the quantity of amplified DNA, detected by fluorescence.

Figure 2A:
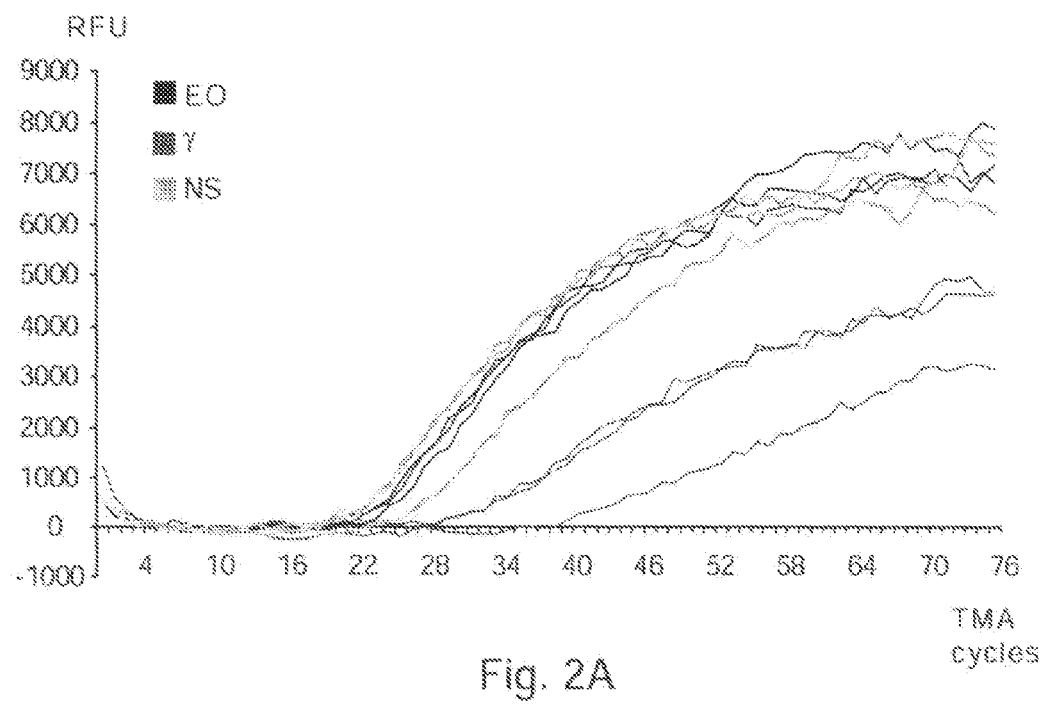
Figure 2B:
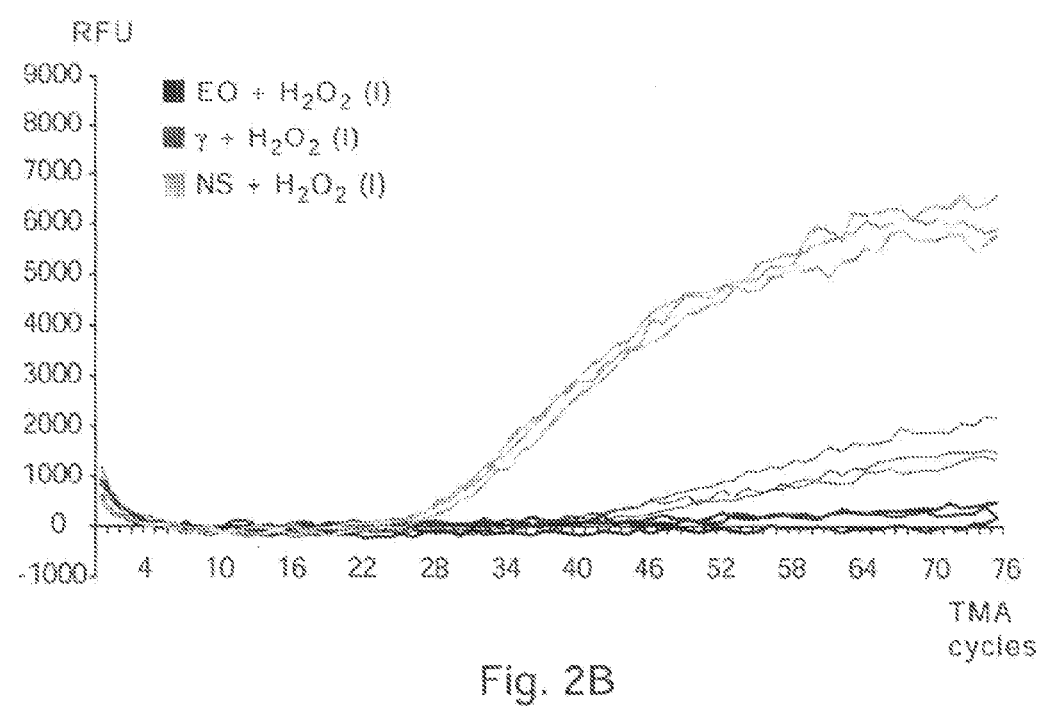

FIG. 2: A graph comparing the different decontamination treatments applied to residual RNA contained initially in microorganisms (P. aeruginosa). The surfaces of the consumables (1.5 ml tubes) were contaminated with the same number of cells of P. aeruginosa before receiving one of the respective treatments. 2A: EO (medium gray): treatment by ethylene oxide in gaseous phase. γ (dark gray): treatment with gamma radiation. NS (light gray): no treatment. 2B: EO+$H_2O_2$ (l) (black): treatment with ethylene oxide in gaseous phase then with hydrogen peroxide in solution (30%). γ+$H_2O_2$ (l) (dark gray): treatment by gamma irradiation then with hydrogen peroxide in solution (30%). NS+$H_2O_2$ (l) (light gray): treatment with hydrogen peroxide in solution (30%) only. NS (light gray): no treatment. The surfaces so treated were then rinsed and a TMA reaction (76 cycles) was carried out on the rinsing products, for the purpose of detecting possible residual RNA coming from P. aeruginosa. The curves represent the quantity of amplified RNA, detected by fluorescence.

Figure 3A:
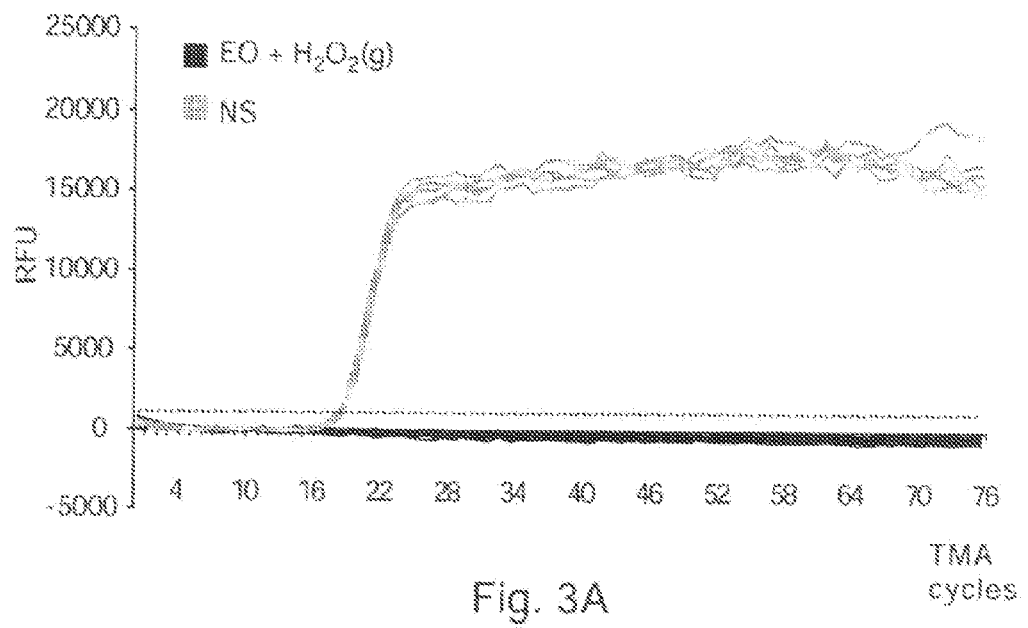
Figure 3B:
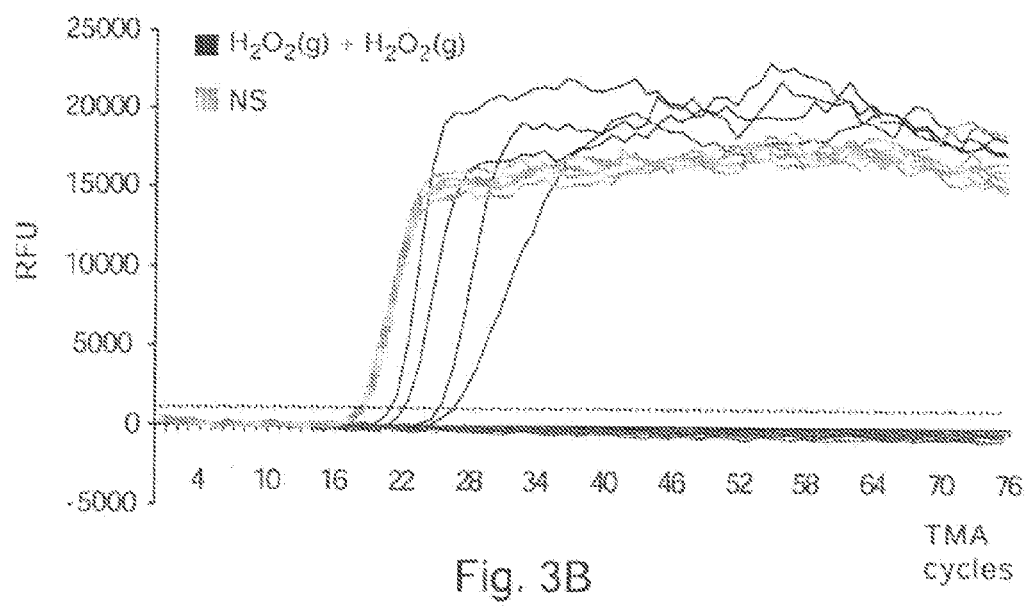

FIG. 3: A graph comparing the different decontamination treatments applied to residual RNA contained initially in microorganisms (P. acnes). The surfaces of the consumables were contaminated with the same number of cells of P. acnes before receiving one of the respective treatments. 3A: EO+$H_2O_2$ (l) (black): treatment by ethylene oxide in gaseous phase then by hydrogen peroxide in gaseous phase (Sterrad®). NS (light gray): no treatment 3B: $H_2O_2$ (g)+$H_2O_2$ (g) (black): treatment comprising two cycles of treatment by hydrogen peroxide in gaseous phase (Sterrad®). NS (light gray): no treatment The surfaces so treated were then rinsed and a TMA reaction (76 cycles) was carried out on the rinsing products, for the purpose of detecting possible residual RNA coming from P. acnes. The curves represent the quantity of amplified RNA, detected by fluorescence.

Figure 4:
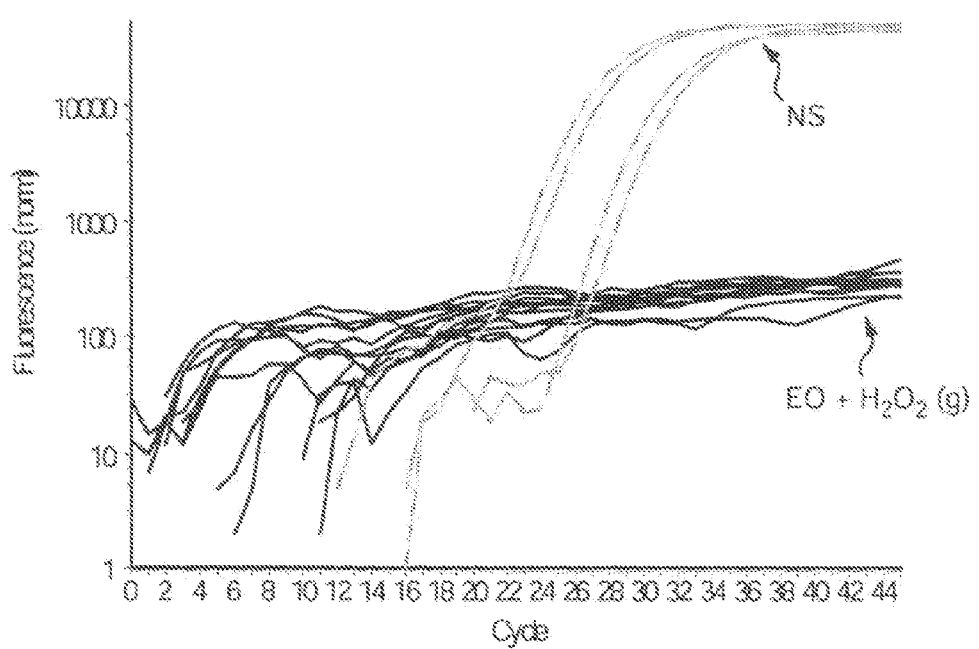

FIG. 4: A graph comparing different decontamination treatments applied to residual DNA contained initially in microorganisms (G. stearothermophilus). The consumables (filter units comprising several filters) were contaminated with the same number of spores of G. stearothermophilus before receiving one of the respective treatments. NS (light gray): no treatment EO+$H_2O_2$ (g) (black): treatment according to the invention with ethylene oxide in gaseous phase then by hydrogen peroxide in gaseous phase (90%).

DETAILED DESCRIPTION

The present invention relates to a method of treatment of the amplifiable residual nucleic acids, that are present on the surface of an object, for example, a consumable product in molecular biology, allying a phase of treatment with gaseous ethylene oxide and a second phase of treatment with hydrogen peroxide in liquid or gaseous phase.

This method preferably comprises the following steps:
 i) Treating the surface of said consumable with ethylene oxide in gaseous phase; then
 ii) Treating said surface with hydrogen peroxide in liquid phase or in gaseous phase.

The term "consumable" is used herein to mean any object used in the manipulation of the nucleic acids, from their collection in the environment to the laboratory, where the amplifications are carried out. The consumable may be made from different materials.

The consumables to which the invention is directed are more particularly filter devices of plastic comprising filter membranes, preferably of polypropylene, PES or PVDF, such as those commercialized by the applicant.

The consumables are more particularly implemented in the context of the manipulations for the purpose of performing nucleic acid amplifications, in particular by means of techniques such as PCR which is preferably performed on the basis of DNA samples, or TMA which is preferably carried out on RNA samples.

The first step i) of the process is generally carried out conventionally [Pittet et al. 1997, Swiss Noso, 4(1)] in a closed chamber (e.g. Steri-Vac 5 XL, 3M) using a concentration of gaseous ethylene oxide preferably greater than 75%, more preferably between 60% and 99%, and still more preferably between 70% and 90% (v/v).

Unless otherwise indicated, the concentrations are as volume per volume percentages (% v/v).

As ethylene oxide is a molecule of small size, its penetration capacity is high, which, among other things, enables treatment of consumables pre-packed in gas-permeable packaging. This penetration capacity explains its high effectiveness in sterilizing complex objects, which are difficult to access. Ethylene oxide also reaches the main constituents of living material (DNA, proteins, vitamins, enzymes), which gives it high sterilizing capacity. Treatment with ethylene oxide is thus active against all living cells and thus has a sterilizing effect. The effectiveness of the treatment is influenced by several parameters: the relative humidity of the gas, which is preferably greater than or equal to 30% and the temperature which is preferably between 40° C. and 60° C., and more preferably between 50° C. and 60° C.

The duration of contact between gaseous ethylene oxide and the surface of the consumables varies between one and six hours, according to the assumed concentration of spores and microorganisms, and the materials from which the consumables are constituted. The treatment in gaseous phase is more effective when, beforehand, the vacuum is applied to the treatment chamber, within or else around the consumable to be treated.

According to the invention, step ii) of treatment with hydrogen peroxide is carried out either in liquid phase, using an aqueous solution, or in gaseous phase.

When the hydrogen peroxide at step ii) is in liquid phase, its concentration is preferably between 25% and 60%. A concentration greater than or equal to 30% has proved to be optimal according to the experiments carried out by the inventors (table 3).

The treatment in liquid phase has the advantage of solubilizing the residual nucleic acids. Furthermore, the passage of a liquid stream through the filters, the case arising, makes it possible to more effectively reach the residual nucleic acids situated in the porous materials that constitute those filters.

The hydrogen peroxide in liquid phase is more effective when it is heated to a temperature between 50° C. and 70° C., preferably greater than 60° C.

This temperature has the advantage of not damaging the materials from which the consumables are constituted.

The hydrogen peroxide, in liquid phase, is generally kept in contact with the surface to be decontaminated, preferably, for a period of at least 40 minutes, preferably between 40 minutes and 1 hour. This period is greater than that for the treatment in gaseous phase described below, and generally requires a drying phase to eliminate the hydrogen peroxide from the surface of the consumables.

The treatment with hydrogen peroxide of step ii) in gaseous phase is generally carried out by vaporization of the hydrogen peroxide, which is preferably brought to a concentration greater than 30%, preferably greater than 50%, and more preferably greater than 80% of the total gas.

The hydrogen peroxide may be passed into the plasma state by application of an electric field, preferably at a temperature below 70° C., more preferably below 60° C., which enables it to be degraded and thus inactivated at the end of the treatment.

The temperatures indicated above are less than for the conventional sterilization processes, better preserve the quality of the materials from which the consumables may be constituted, in particular, the membranes or filters which may compose them.

Such a process may be implemented in devices dedicated to treatments using hydrogen peroxide in gaseous phase, such as the Sterrad® process (ASP-Johnson & Johnson), in accordance with the recommendations of the manufacturers of those devices.

The Sterrad® process constitutes a possible but non-limiting embodiment of step ii). The implementation of the hydrogen peroxide in gaseous phase has the advantage of being able to be applied to consumables pre-packed in gas-permeable packaging. Thus, when the two steps of the process according to the invention are carried out in gaseous phase, the consumable may be packaged or pre-packed before undergoing these two steps.

Similarly, when the treatment with hydrogen peroxide is carried out in gaseous phase, steps i) and ii) may succeed each other in the same treatment chamber, which limits the contact of the consumables with the residual nucleic acids of the surroundings.

The results obtained by the inventors are illustrated below in the examples of the application. FIGS. 1 to 4 show that the process according to the invention makes it possible to obtain a more effective treatment of the residual nucleic acids, whatever their origin (cellular or free), their nature (RNA or DNA) or the mode of amplification envisioned (PCR or TMA). Such a level of effectiveness results from the combination of steps i) and ii) according to the invention and from the order in which they are carried out.

The process according to the invention results in a treated consumable, that is free from amplifiable nucleic acids, which it was not possible to obtain previously, in particular as regards the consumables comprising one or more filters or membranes, preferably of polypropylene, PES or of PVDF.

The invention thus, in particular, enables a consumable to be obtained in molecular biology, whether it be simple or complex, that is free from nucleic acids of bacterial origin (guaranteed DNA free).

EXAMPLES

Protocol 1

Several consumables consisting of 1.5 ml polypropylene tubes were contaminated in parallel with a known quantity of DNA, RNA or microorganisms. These consumables were then gamma-sterilized (doses from 0 to 60 kGy) or treated with ethylene oxide in gaseous phase. After sterilization, the presence of residual nucleic acids is determined by PCR (for DNA) and TMA (for RNA) and compared with an unsterilized control consumable.

The results obtained have been summarized in table 1 below.

TABLE 1

Effectiveness of the residual nucleic acid treatments carried out by means of ethylene oxide (EO) and by means of gamma radiation

| Type | Microorganisms tested | Gamma | EO |
|---|---|---|---|
| DNA (PCR) | E. coli | +++ | + |
| | P. aeruginosa | Degradation of the DNA (30-40 kGy) | Partial degradation |
| RNA (TMA) | P. acnes | + | +++ |
| | P. aeruginosa | Partial degradation | Degradation |
| Germs (PCR) | E. coli | + | + |
| | P. aeruginosa | Dose must be greater than 60 kGy | Partial degradation |

TABLE 1-continued

Effectiveness of the residual nucleic acid treatments carried out by means of ethylene oxide (EO) and by means of gamma radiation

| Type | Microorganisms tested | Gamma | EO |
|---|---|---|---|
| Germs (TMA) | P. acnes | – | – |
| | P. aeruginosa | Little effect (depending on the microorganisms) | No effect |

These results show that the gamma treatment does not fully degrade the RNA contained in microorganisms, nor that in free form. As for the DNA, this is only partially degraded. The treatment with ethylene oxide is effective against RNA in free form, but has no effect on the RNA contained in the microorganisms.

Protocol 2

Several consumables of the same type as those used in protocol 1 were contaminated with the same known quantity of DNA, RNA or microorganisms. These consumables were then treated by a treatment with hydrogen peroxide made in liquid solution (respectively 3% and 30% $H_2O_2$). The hydrogen peroxide is evaporated at the end of the process by virtue of a step of drying under vacuum at a temperature of 60° C. After treatment, the presence of residual nucleic acids was determined by PCR (for DNA) and TMA (for RNA) and compared with an untreated sample.

The results obtained have been summarized in table 2 below, in which (–) signifies no effect, (++) signifies partial degradation of the nucleic acids and (+++) signifies their complete degradation.

TABLE 2

Effectiveness of the residual nucleic acid treatments carried out by means of hydrogen peroxide in 3% and 30% solution

| | Microorganisms tested | $H_2O_2$ 3%* | $H_2O_2$ 30%* |
|---|---|---|---|
| DNA (PCR) | E. coli P. aeruginosa | ++ | +++ |
| RNA (TMA) | P. acnes P. aeruginosa | ++ | +++ |
| Germs (PCR) | E. coli P. aeruginosa | – | – |
| Germs (TMA) | P. acnes P. aeruginosa | – | – |

*Minimum time of action on nucleic acids 40 min at 60° C.

These results show that a concentration of $H_2O_2$ of 30% enables free nucleic acids to be degraded more effectively than a concentration of 3% $H_2O_2$. Nevertheless, the treatment has no effect on nucleic acids contained in the microorganisms.

Protocol 3 (According to the Invention)

Several consumables of the same type as those used in protocol 1 were contaminated with the same known quantity of DNA, RNA or microorganisms. A proportion of those consumables was then treated according to the invention with gaseous ethylene oxide followed by the 3% or 30% hydrogen peroxide. A further proportion was treated with gamma radiation instead of with the gaseous ethylene oxide then with hydrogen peroxide. In both cases, the hydrogen peroxide was evaporated by virtue of a vacuum drying step at a temperature of 60° C. After treatment, the presence of residual nucleic acids was determined by PCR (for DNA) and TMA (for RNA) and compared with an untreated sample.

The results obtained have been summarized in table 3 below, in which (–) signifies no effect, (++) signifies a partial degradation of the nucleic acids and (+++) signifies their complete degradation. These results show that, to a certain extent, the gamma+$H_2O_2$ treatment enables the nucleic acids to be degraded, but the performance of this process is less good than the EO+$H_2O_2$, in particular for the RNA contained in the microorganisms. The treatment by ethylene oxide followed by 30% hydrogen peroxide solution enables the DNA and RNA contained in the microorganisms to be degraded completely, whereas the same treatment but with only 3% $H_2O_2$ is less effective on the DNA and does not work at all on the RNA.

TABLE 3

Effectiveness of the treatments of the residual nucleic acids contained in microorganisms.

| | Gamma + $H_2O_2$ 3%* | Gamma + $H_2O_2$ 30%* | Ethylene oxide + $H_2O_2$ 3%* | Ethylene oxide + $H_2O$ 30%* | Microorganisms tested |
|---|---|---|---|---|---|
| Germs (PCR) | + Reduces positivity level | +++ | + Reduces positivity level | +++ | E. coli P. aeruginosa |
| Germs (TMA) | + Reduces positivity level | ++ Variably effective | – Little or no effect | +++ | P. acnes P. aeruginosa |

*Contact for 1 h at 60° C.

Protocol 4

Several complex consumables comprising several filters were contaminated with the same known quantity of microorganisms (G. stearothermophilus). A proportion of those consumables was then treated according to the process of the invention with gaseous ethylene oxide then the gaseous hydrogen peroxide at approximately 90%. A further proportion of the consumables serving as a control was not treated. The presence of residual nucleic acids (DNA) was determined by PCR. FIG. 4 records the quantities of DNA amplified during the different PCR cycles. The absence of amplification in the treated samples may be noted.

The invention claimed is:

1. A method of eliminating amplifiable residual nucleic acids present on the surface of a consumable, comprising:
    i) Treating the surface of said consumable with ethylene oxide in gaseous phase; then
    ii) Treating said surface with hydrogen peroxide in liquid phase or in gaseous phase.

2. A method according to claim 1, wherein the ethylene oxide at step i) is used with a concentration of between 70% and 90% (v/v).

3. A consumable treated according to the method of claim 2, wherein it is free of amplifiable residual nucleic acids.

4. A method according to claim 1 or 2, wherein the hydrogen peroxide is in liquid phase at a concentration between 25% and 60% (v/v).

5. A method according to claim 2 or 4, wherein the hydrogen peroxide, in liquid phase, is in contact with the surface to be decontaminated for a period of at least 40 minutes.

6. A method according to claim 4, wherein the hydrogen peroxide in liquid phase is heated to a temperature between 50° C. and 70° C.

7. A method according to claim 1, wherein the treatment with hydrogen peroxide is carried out in gaseous phase.

8. A method according to claim 7, wherein the hydrogen peroxide is vaporized, then brought to a concentration greater than 30%.

9. A method according to claim 8, wherein the hydrogen peroxide is passed into the plasma state by application of an electric field at a temperature below 60°.

10. A method according to claim 1, further comprising an evaporating step after treating said surface with said ethylene oxide but before treating said surface with said hydrogen peroxide.

11. A method according to claim 1, wherein the consumable in molecular biology is packaged beforehand in a partially nonwoven pack.

12. A method according to claim 1, wherein vacuum is applied before treating said surface with said ethylene oxide or before treating said surface with said hydrogen peroxide.

13. A method according to claim 1, wherein the residual ethylene oxide is eliminated after treating said surface with said ethylene oxide but before treating said surface with said hydrogen peroxide.

14. A method according to claim 1, wherein the residual hydrogen peroxide is eliminated from the surface of the consumable after treating said surface with said hydrogen peroxide.

15. A consumable treated according to the method of claim 1, wherein it is free of amplifiable residual nucleic acids.

16. A consumable according to claim 15, wherein said consumable comprises a filter or a membrane, which filter or membrane is of polypropylene, PES or PVDF.

* * * * *